(12) United States Patent
Fortuna et al.

(10) Patent No.: US 10,772,593 B2
(45) Date of Patent: Sep. 15, 2020

(54) RESTRAINING DEVICE FOR RADIOLOGICAL EXAMINATIONS

(71) Applicant: IMAGINALIS S.R.L., Sesto Fiorentino (Firenze) (IT)

(72) Inventors: Damiano Fortuna, Rignano sull'Arno (IT); Leonardo Manetti, Montevarchi (IT)

(73) Assignee: Epica International, Inc., San Clemente, CA (US)

( * ) Notice: Subject to any disclaimer, the term of this patent is extended or adjusted under 35 U.S.C. 154(b) by 79 days.

(21) Appl. No.: 15/778,221

(22) PCT Filed: Nov. 18, 2016

(86) PCT No.: PCT/IB2016/056949
§ 371 (c)(1),
(2) Date: May 22, 2018

(87) PCT Pub. No.: WO2017/089934
PCT Pub. Date: Jun. 1, 2017

(65) Prior Publication Data
US 2018/0344277 A1 Dec. 6, 2018

(30) Foreign Application Priority Data
Nov. 24, 2015 (IT) .............................. UB2015A5854

(51) Int. Cl.
*A61B 6/00* (2006.01)
*A61B 6/04* (2006.01)
(Continued)

(52) U.S. Cl.
CPC ............ *A61B 6/508* (2013.01); *A61B 6/0421* (2013.01); *A61D 3/00* (2013.01); *A61B 6/03* (2013.01); *A61N 2005/1097* (2013.01)

(58) Field of Classification Search
None
See application file for complete search history.

(56) References Cited

U.S. PATENT DOCUMENTS 3,250,252 A * 5/1966 Seymour .............. A01K 1/0613
119/756
6,666,169 B2 * 12/2003 Dehod ................. A01K 1/0606
119/731
(Continued)

FOREIGN PATENT DOCUMENTS

JP S57-86827 A 5/1982
JP H02-297343 A 12/1990
(Continued)

OTHER PUBLICATIONS

Stephanie Dakin, "Technical set-up and radiation exposure for standing computed tomography of the equine head" Apr. 1, 2014, Equine Veterinary Education, p. 208-215 (Year: 2014).*
(Continued)

*Primary Examiner* — David R Hare
*Assistant Examiner* — Adam C Ortiz
(74) *Attorney, Agent, or Firm* — Steptoe & Johnson LLP

(57) ABSTRACT

A supporting device for performing radiological examinations on a patient having a part of the body examined includes perimeter side members, an openable containment portion, and an examination portion. The perimeter side members are configured to contain the patient along a closed perimeter and at least in a horizontal plane and substantially in contact, when in use, on a plurality of sides of the perimeter with the patient. The openable containment portion is formed by most of the perimeter side members. The examination portion is formed by the remainder of the (Continued)

perimeter side members, is substantially transparent to X-rays, and is configured to contain the part of the body to be examined.

9 Claims, 5 Drawing Sheets

(51) Int. Cl.
    *A61D 3/00*      (2006.01)
    *A61B 6/03*      (2006.01)
    *A61N 5/10*      (2006.01)

(56) References Cited

U.S. PATENT DOCUMENTS 8,292,505 B2 * 10/2012 Tybinkowski ......... A61B 6/032
                                                                               378/209
2006/0169220 A1 * 8/2006 Kerns ................. A01K 1/0606
                                                                               119/732
2009/0090306 A1 * 4/2009 Miles ................... A01K 1/0613
                                                                               119/732

FOREIGN PATENT DOCUMENTS

| JP | H03-94737 A | 4/1991 |
| JP | 2002-35017 A | 2/2002 |
| JP | 3639896 B2 * | 4/2005 |

OTHER PUBLICATIONS

The International Search Report and Written Opinion of the International Searching Authority, PCT/IB2016/056949, dated Feb. 6, 2017.

* cited by examiner

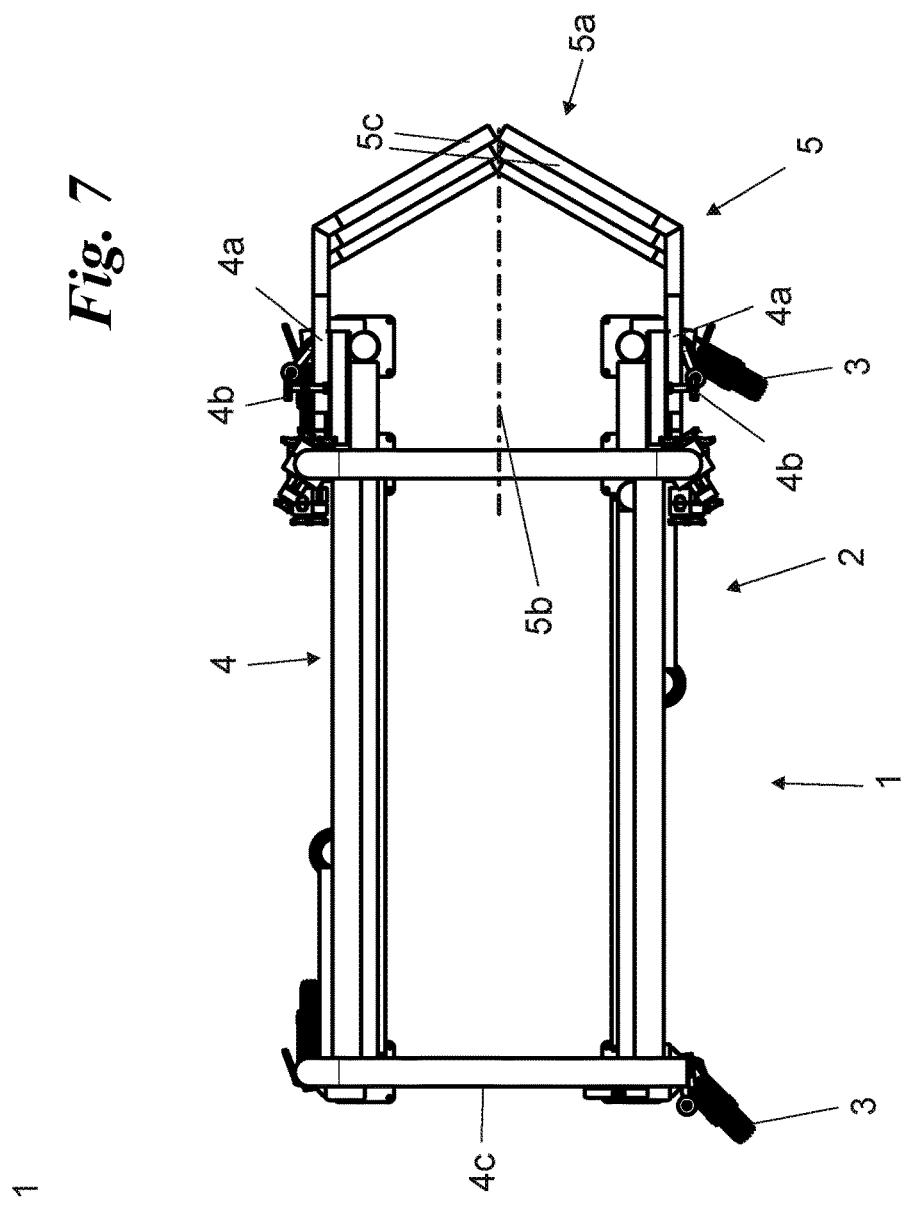
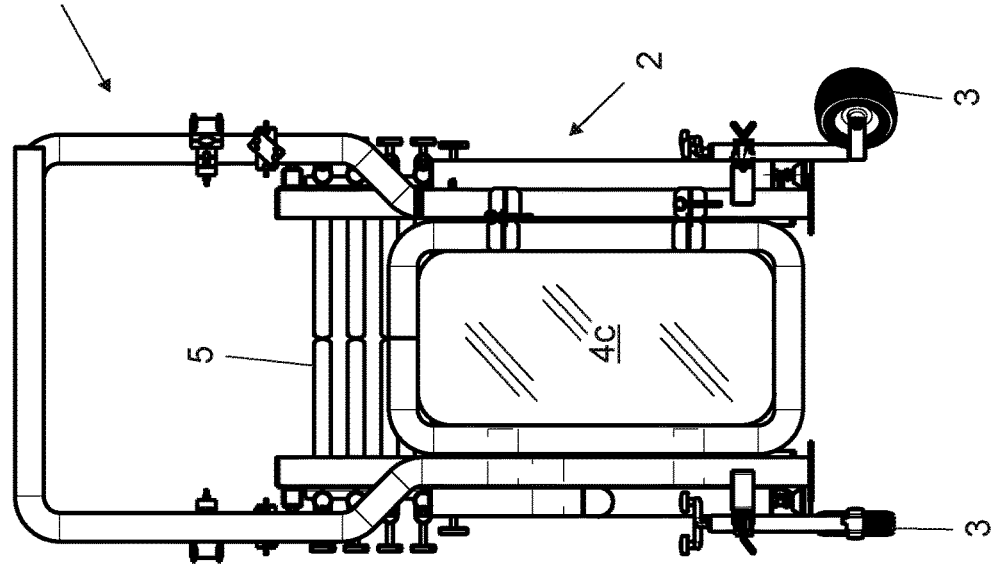

ial Patent Application No. UB2015A005854, filed Nov. 24, 2015, each of which is incorporated by reference in its entirety.

RESTRAINING DEVICE FOR RADIOLOGICAL EXAMINATIONS

CROSS-REFERENCE TO RELATED APPLICATIONS

This application is a National Stage Filing based on and claims priority from International Application No. PCT/IB2016/056949, filed Nov. 18, 2016, which claims priority from Italian Patent Application No. UB2015A005854, filed Nov. 24, 2015, each of which is incorporated by reference in its entirety.

FIELD OF THE INVENTION

The present invention relates to a supporting device for performing radiological examinations. In particular, the present invention concerns a device suitable for use in radiology and, in particular, in the veterinary field to support a patient, preferably an animal, in the correct position during radiological imaging. In addition, the supporting device is suitable for use in a radiological-intraoperative operation.

BACKGROUND

At present, beds or similar devices are used to support the patient during radiography. Such beds consist of a flat structure that defines the supporting surface on which the patient is placed, and means for anchoring the flat structure to a radiological imaging device. With such beds, the patient, in particular, the animal, is placed on the bed so as to assume the correct position and so that the region of interest for acquiring an image is inside the examination area, that is to say, between the sensor and the source. The patient is blocked in this position by means of belts or straps to prevent it from moving and thus not permitting the correct acquisition of the image of the region of interest. Note that, to prevent such movements, the animal is often sedated.

The prior art described above has several significant drawbacks.

A first important drawback lies in the fact that with such beds, arranging the animal in the correct position is a complicated and laborious process. This problem is particularly evident in the case of horses or other large animals that are difficult to place on the bed.

Another important drawback is that since the image must be acquired with the animal lying down, this limits the possibility of seeing defects and problems. This aspect is made worse by the fact that belts or straps are often used to prevent the animal from moving and, since these pass over the region of interest, they undermine the quality of the image acquired.

Another no less important drawback lies in the fact that the animal almost always has to be sedated.

SUMMARY

In this situation the technical purpose of one embodiment of the present invention is to devise a supporting device for radiological examinations able to substantially overcome the drawbacks mentioned above. Within the sphere of said technical purpose one important aim of this embodiment is to provide a supporting device for radiological examinations that is both easy and simple to use. Another important aim of this embodiment is to provide a supporting device for radiological examinations that allows the image to be acquired easily even if the animal is not lying down. A further purpose of this embodiment is to provide a supporting device for radiological examinations that allows images to be acquired while holding the animal still without using elements that could interfere with the acquisition of the image.

BRIEF DESCRIPTION OF THE DRAWINGS

The various embodiments will now be shown with the following detailed description of an exemplary embodiment of a supporting device for radiological examinations, with reference to the attached drawings in which:

FIG. 6 shows a rear view of the supporting device according to the embodiment of FIG. 1; and FIG. 7 shows a view from above of the supporting device according to the embodiment of FIG. 1.

DETAILED DESCRIPTION

Figure 1:
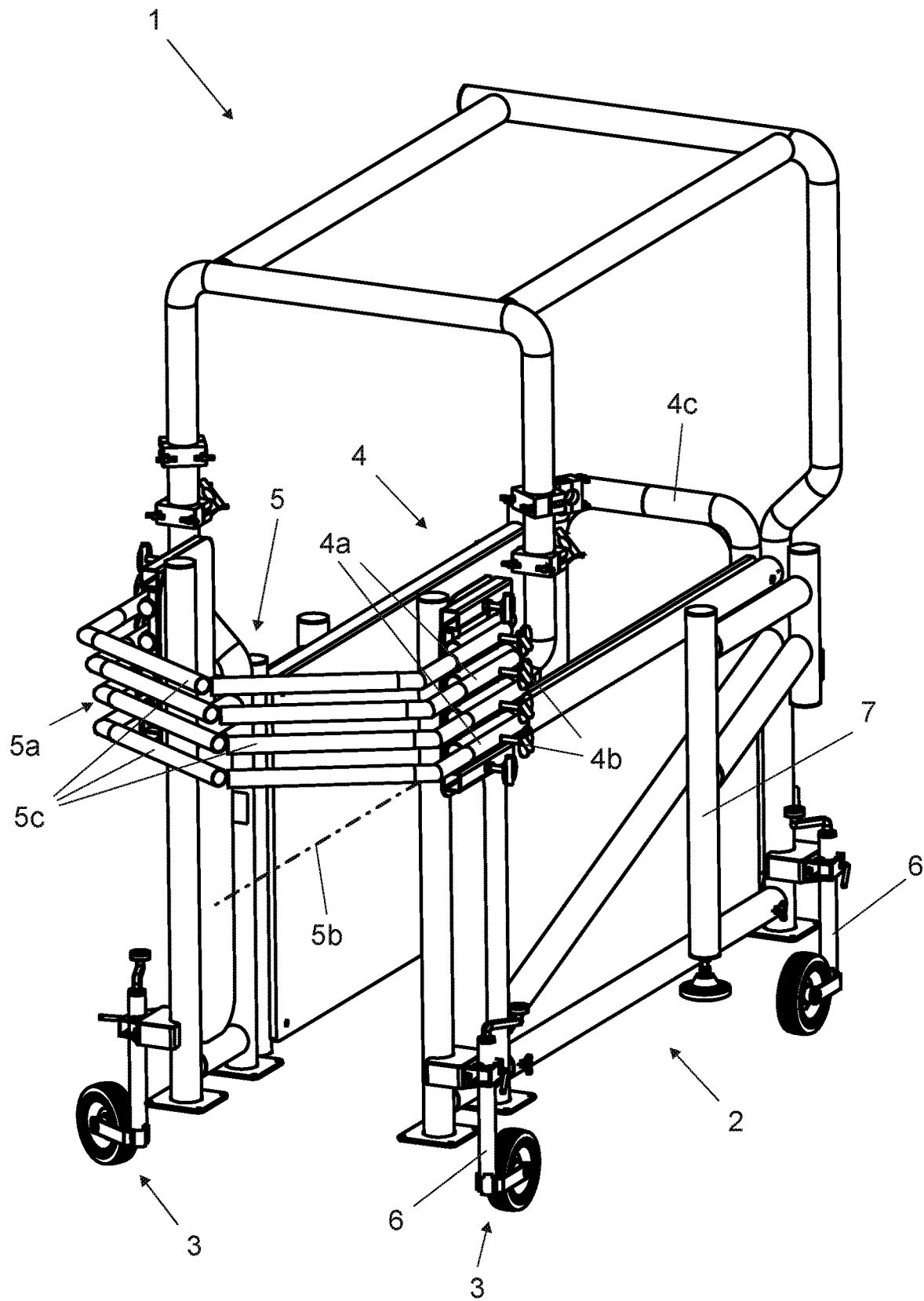
FIG. 1 shows a first axonometric view, mainly from the front, of the supporting device according to an embodiment of the invention.
Figure 2:
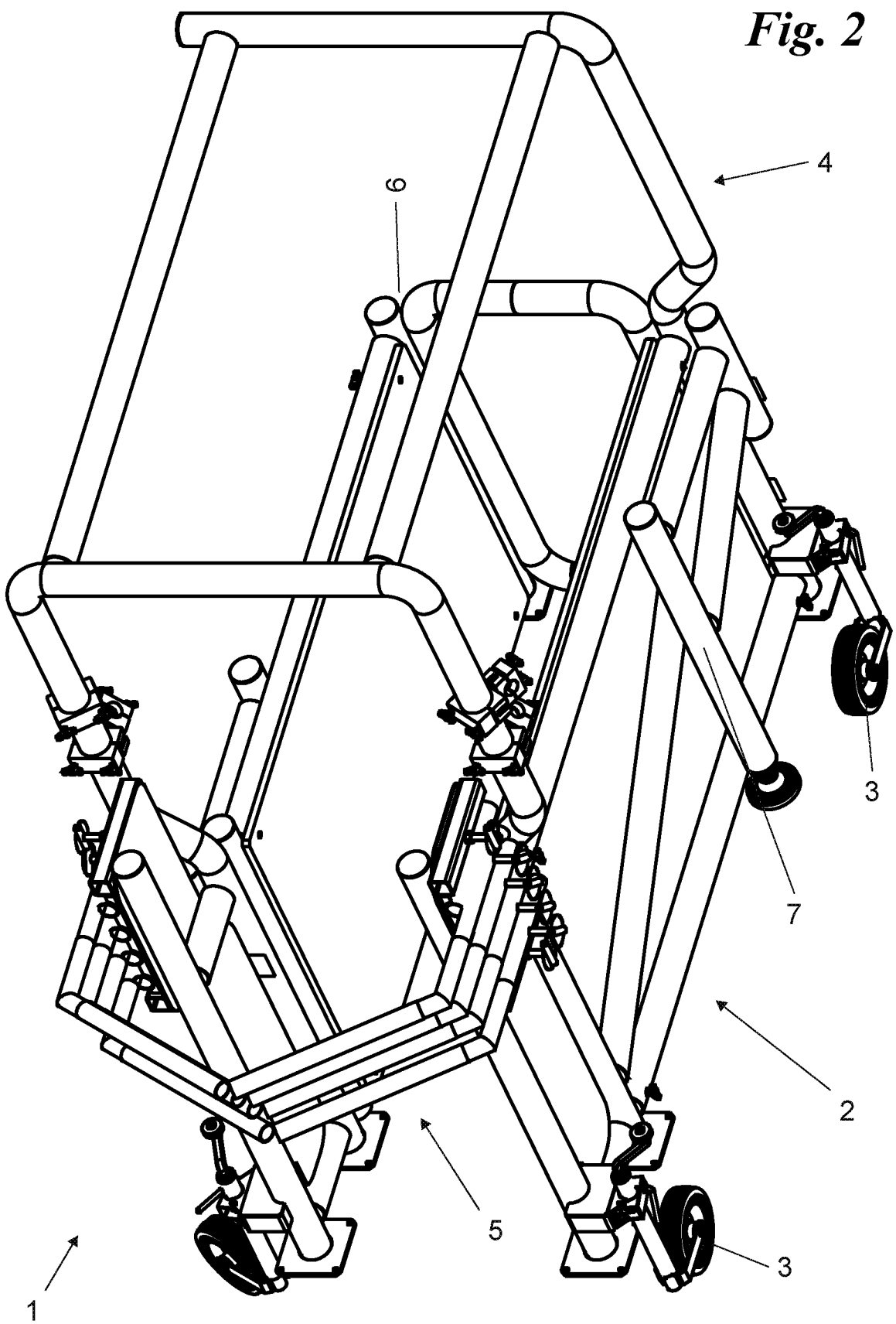
FIG. 2 shows a second axonometric view, mainly from above, of the supporting device according to the embodiment of FIG. 1.
Figure 3:
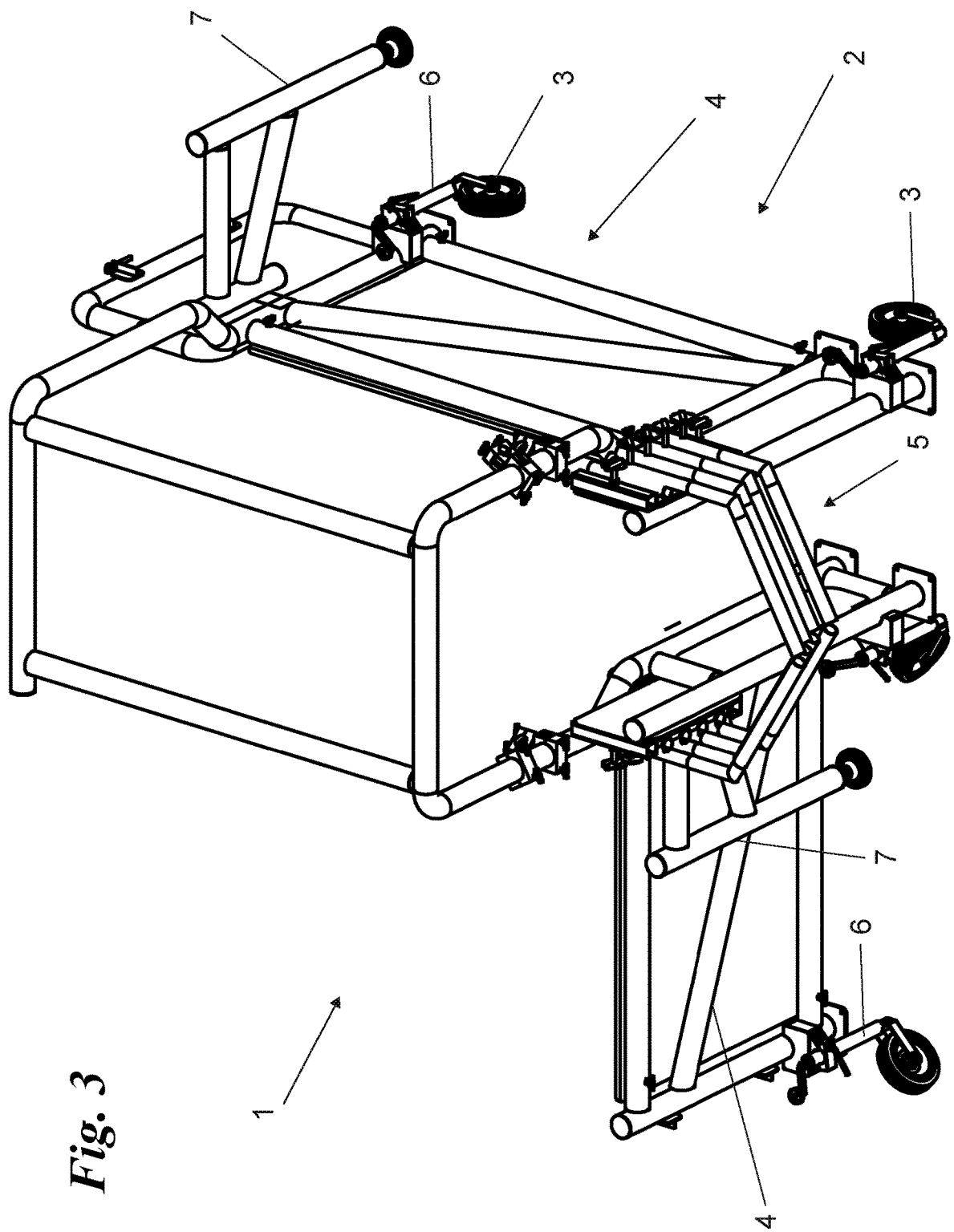
FIG. 3 shows an axonometric view, mainly from above and in a second configuration, of the supporting device according to the embodiment of FIG. 1.
Figure 4:
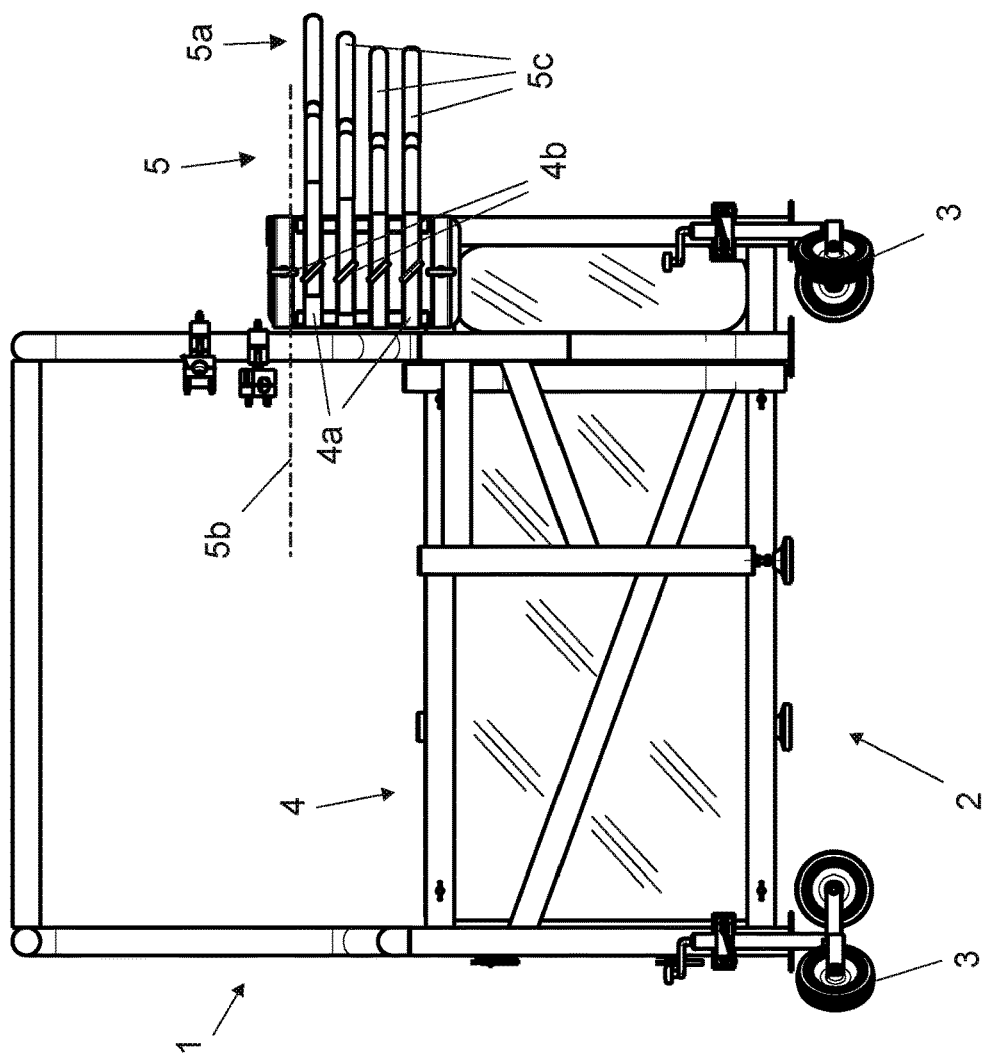
FIG. 4 shows a side view of the supporting device according to the embodiment of FIG. 1.
Figure 5:
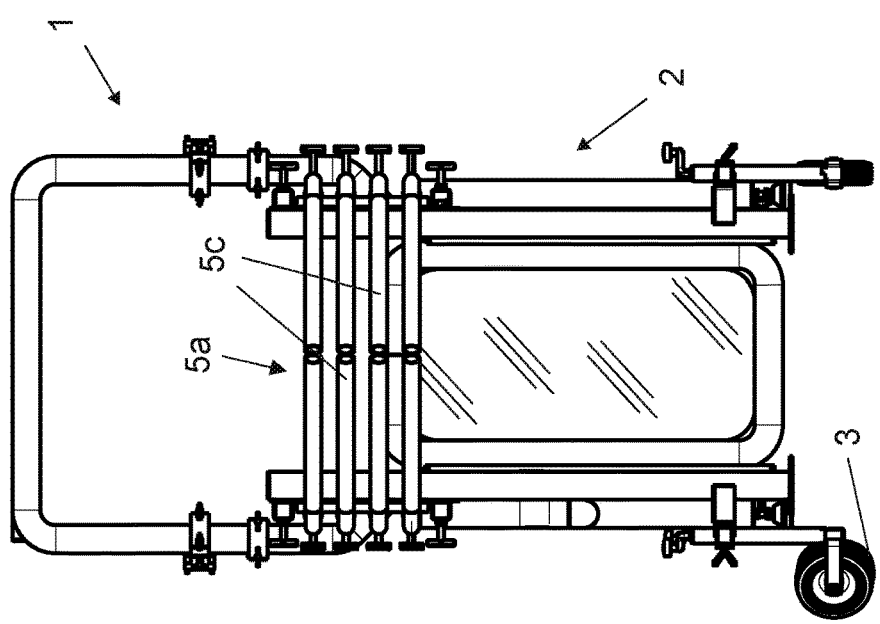
FIG. 5 is a front view of the supporting device according to the embodiment of FIG. 1.

In this document, measurements, values, forms and geometric data (such as perpendicularity and parallelism), when used with terms such as "about" or other similar terms such as "practically" or "substantially", are to be considered without any measurement errors or inaccuracies due to production and/or manufacturing errors and, above all, without any slight divergence from the value, measurement, form or geometric data with which they are associated. For example, such terms, when associated with a value, preferably indicate a difference of not more than 10% of said value.

Moreover, terms such as "first", "second", "upper", "lower", "main" and "secondary" do not necessarily indicate an order, priority or respective position, but may simply be used in order to make a clear distinction between the different components.

With reference to said figures, reference numeral 1 globally denotes the supporting device for radiological examinations according to an embodiment of the invention. It is suitable for blocking, immobilising, or simply limiting the space occupied by a patient and the movements thereof during a radiological examination. Said patient is preferably an animal, more preferably a quadruped and even more preferably an equine or bovine, yet more preferably a horse. Said patient thus has a part of its body that needs to be examined, in the specific case this may be a leg or the head or neck or other part of the body.

The supporting device 1 is thus suitable for use in radiological examinations, in particular to perform a tomography, radiography and/or fluoroscopy on said patient and on said part of the body. The supporting device 1 is, thus, suitable for use with a radiological imaging device. In detail, it can be at least partially inserted inside the examination area of the radiological imaging device, that is to say, between the source and the detector of said radiological imaging device.

The supporting device 1 comprises, in brief, perimeter side members 2 suitable for containing the patient along a closed perimeter and at least in the horizontal plane and with which the patient preferably comes into contact on a plurality of sides of the perimeter.

Note that, in this document, the term "horizontal" refers to a plane, an axis substantially parallel to the floor and, in particular, substantially perpendicular to the gravitational gradient. Moreover, in this document the term "vertical" refers to a plane, an axis substantially perpendicular to the floor and, in particular, substantially parallel to the gravitational gradient.

Essentially, the perimeter side members 2 surround the patient in the horizontal plane, appropriately entirely, so that the patient is constrained inside them. The side members 2 thus come into contact with the patient on several sides and, preferably, on at least the four sides defined by orthogonal planes.

Appropriately, furthermore, the supporting device 1 need not comprise a base or bases or horizontal supports to support the patient, so that the latter stands directly on the floor.

The perimeter side members 2 comprise a containment portion 4, appropriately openable, formed by most of said perimeter side members 2, and an examination portion 5 formed at least partially by and, in particular, practically all of the remainder of the perimeter side members 2, suitable to contain the part of the body to be examined and substantially transparent to X-rays.

In more detail, the examination portion 5 protrudes, in the horizontal plane, with respect to the containment portion 4. As a consequence, the examination portion 5 forms a portion that, in the horizontal plane or when seen from above, is exclusively made of material that is substantially transparent to X-rays and which can thus be inserted, preferably practically exclusively, inside the examination area of a radiological imaging device.

In particular, the examination portion 5 protrudes in a direction of exposure 5$b$ with respect to the containment portion 4, and along a surface approximately perpendicular to said direction of exposure 5$b$. As a consequence, the perimeter side members 2 delimit a housing for the patient, and the examination portion 5 delimits a portion of said housing that is distinct from that delimited by the containment portion 4. Said direction of exposure 5$b$ is substantially horizontal.

Furthermore, advantageously, the examination portion 5 defines an examination wall 5$a$ that is substantially wedge-shaped in the horizontal plane or when seen from above. Said wedge portion allows the part of the body to be examined to be blocked in an exact position in correspondence with the middle corner of said wedge. Clearly, said wedge is convex, appropriately having the concavity facing inwards, that is to say towards the containment portion 4, as illustrated in the accompanying figures. Said examination wall 5$a$ is preferably translatable, in the horizontal plane, in the direction of exposure 5$b$, so that a larger or smaller area can be selected for the examination portion 5.

Moreover, the examination portion 5 is formed by a plurality of elements 5$c$ that are stacked vertically but preferably so as not to come into contact with one another, and each of which can be moved and/or extracted separately and independently of the other said elements 5$c$. Preferably, said elements 5$c$ are tubular or similarly shaped and comprise a first wedge portion and at least a second portion, appropriately one for each of the two ends of the wedge, parallel to the direction of exposure 5$b$. The latter second portion may be arranged in seats 4$a$ provided in the containment portion 4. Said seats 4$a$ are substantially slots or coupling sleeves and comprise locking elements 4$b$, such as screws or the like. The elements 5$c$ may also be divided in a sagittal plane into two separate portions that touch one another or are a very small distance apart in correspondence with the central part of said wedge portion.

It is highlighted that each of the elements 5$c$ can be rotated around an axis of rotation substantially parallel to the direction of exposure 5$b$. In particular, the elements 5$c$ can be rotated independently so as to be mutually pushed together or apart. Alternatively, they are synchronously rotatable.

Lastly, the examination portion 5 is appropriately made of a material that is transparent to X-rays, and preferably with a radiodensity of, on average, substantially less than 1000 HU (Hounsfield units), less than 600 HU and, more preferably, less than 100 HU. It is preferably made of a composite material with a polymeric matrix and, appropriately, an epoxy matrix. The polymeric matrix may be a resin and more preferably epoxy or similar resin. Alternatively, the matrix is foam, appropriately epoxy foam. A reinforcement is preferably in the form of fibre, more in detail, carbon fibre or aramid fibre.

Thanks to said mobility of the elements 5$c$, the examination wall 5$a$ is substantially variable in shape and may be adjusted according to the specific animal and the specific part of the body to be examined.

To sum up for the sake of clarity, the perimeter side members 2 delimit a housing that is more or less parallelepiped in shape, one face of which, preferably approximately wedge shaped as described above, consists of the examination wall. Of such parallelepiped housing with a wedge-shaped face, the containment portion 4 substantially defines three side walls of the parallelepiped, and the examination portion 5 defines the remainder of the parallelepiped, that is to say, the part delimited by the wedge-shaped face.

As previously mentioned, the containment portion 4 is openable, so that the patient can easily be placed inside. The opening is preferably wide and preferably regards an angular portion of the perimeter, in the horizontal plane or as seen from above, having an angle of more than 90°, more preferably more than 120°, even more preferably more than 150° and less than 200°.

In detail, the containment portion 4 preferably comprises two consecutive side members out of three that are openable. Preferably the openable side members are a rear side member 4$c$, opposite the examination wall 5$a$, and a side wall. Appropriately, the containment portion 4 has the two side walls opposite one another and adjacent to the rear side member 4$c$ arranged at a distance between them such as to allow the patient to be placed between the perimeter side members 2 in the standing position. Said distance between said opposite side walls, calculated perpendicularly to the direction of exposure 5$b$, is substantially less than 2 m and, in detail, less than 1.5 m and, in more detail, less than 1 m. To be precise, the distance between opposite side walls is substantially between 0.7 m and 0.3 m and, preferably, between 0.6 m and 0.5 m.

The containment portion 4 may also comprise an upper side member, substantially horizontal and preferably fastened to the remaining part of the containment portion 4 by means of releasable fastening means. Structurally the containment portion 4 preferably consists of a trellis structure preferably consisting of hollow tubular elements. Said trellis structure is preferably made of metal and can be filled with flat elements, made for example of wood, polymer or even metal. It may also comprise a padding made of a soft material, such as polymer, elastomer or other material.

The supporting device 1 for radiological examinations is connected to and supported by a radiological imaging device. According to a preferred alternative embodiment, the supporting device 1 stands on the floor. In detail, the device 1 may be supported statically, that is to say, so that it cannot be moved, or preferably, the device 1 is mobile and may thus comprise sliding means 3 suitable to allow the supporting device 1 to be moved with respect to the floor along the horizontal plane. The sliding means 3 comprise wheels, preferably pivoting wheels. They appropriately engage with the structure in the containment portion 4 so as not to be superimposed on the examination portion 5. The sliding means 3 are appropriately removable. The term "removable" refers to the fact that the supporting device 1 may be movable, meaning placed in contact with the floor practically exclusively through the sliding means 3; or substantially approximately anchored to the floor when the sliding means 3 are not in contact with the floor.

To sum up, the fact that the sliding means 3 are removable refers to the fact that the sliding means 3 can be removed/detached from the supporting device 1 and, thus, has no sliding means 3 and is substantially and approximately anchored to the floor. Therefore, the supporting device for radiological examinations 1 may comprise attachments suitable to fix or remove the sliding means 3 with respect to the rest of the device 1.

Alternatively, saying that the sliding means 3 are removable refers to the fact that fixed supports can extend vertically downwards beyond the sliding means 3. In that case, the supporting device 1 may comprise linear movement devices 6, preferably one for each of the sliding means 3, suitable to move the sliding means 3 along a vertical axis with respect to the containment portion 4 so as to allow the device 1 to selectively be movable or practically approximately anchored to the floor. The linear movement devices 6 may be controlled synchronously so that all of the means 3 move simultaneously in the vertical direction and by the same distance. Alternatively, the linear movement devices 6 may be controlled independently so as to obtain a specific vertical displacement of each of the means 3 and thus tilt the device 1 with respect to the floor. Each linear movement device 6 may comprise a screw mechanism, that is to say, a hollow duct with vertical internal thread integral with the perimeter side members 2 and a screw extending vertically and integral with the sliding means 3 and engaging said internal thread; and a crank for controlling said screw suitable to control a rotation of the screw with respect to said hollow duct and, thus, a vertical translation of the means 3.

The supporting device for radiological examinations 1 may further comprise lateral supports 7 preferably structurally similar to the perimeter side members 2 and in particular made of hollow tubular trellises. The lateral supports 7 protrude from the perimeter side members 2 and act as stabilisers for the supporting device for radiological examinations 1. They are preferably movably joined to the perimeter side members 2 and, specifically, to the containment portion 4, in particular by means of hinges with a vertical axis of rotation, so that they can be arranged alongside the perimeter side members 2 or arranged in a supporting position protruding from the perimeter side members 2. The lateral supports 7 are preferably at least two and, more preferably, two in number and opposite one another, for example arranged at two opposite corners of the rectangular base formed by the parallelepiped described earlier, as illustrated in the accompanying figures.

Lastly, the supporting device 1 may comprise retaining means integral with the floor, such as screws or specific hooks, to ensure its safe fastening.

Additionally the supporting device 1 may comprise a retainer adapted to prevent undesired movements of the patient and, in particular, to maintain substantially stationary at least the portion to be analyzed. The retainer is adapted to press the patient against the examination wall 5a. It is bound to the containment portion 4, preferably, labile so as to be able to translate with respect to the same containment portion 4 along the direction of exposure 5b. In particular, the retainer is constrained in a solvable manner to the containment portion 4.

In detail, the retainer is constrained to the containment portion 4 in correspondence of opposite side members that are parallel to the direction of exposure 5b. In more detail, the retainer is constrained to sections of said opposite side members substantially parallel to the direction of exposure 5b so as to slide along them and, therefore, said direction 5a approaching and/or loosening from the examination wall 5a. The retainer comprises at least one section bar substantially perpendicular to the direction of exposure 5b; and, preferably, a padding made of a soft material, such as polymer, elastomer or other material.

The functioning of a supporting device 1, described above in a structural sense, is as follows. First, the supporting device for radiological examinations 1 is brought to the radiological imaging device and the examination portion 5 is placed inside the examination area of the radiological imaging device, that is to say between the source and the detector of said radiological imaging device (for example in the examination area defined by a gantry). Next, the sliding means 3 are removed, as described (for example through the vertical lifting of the sliding means 3 from the floor by the linear movement devices 6) and, preferably, the lateral supports 7 are turned outwards to make the supporting device stable.

The supporting device for radiological examinations 1 is fastened securely in place and the radiological examination can be carried out. To insert the patient, the containment portion 4 is opened and the patient led approximately inside. The patient is arranged so that the part to be examined is in the examination portion 5 and, thus, in said examination area. The perimeter side members 2 of the containment portion 4 are then closed and the patient is held tightly in place within the perimeter side members 2 and cannot move except with said side members 2. The part of the body to be examined is wedged inside the examination portion 5 against the wedge-shaped examination wall 5a. Furthermore, said wall is controlled and adjusted by moving and/or removing the elements 5c.

Note that with the supporting device for radiological examinations 1 the patient can be standing up and thus not lying down.

Alternatively, the patient may be first placed inside the supporting device 1 which can then be used to transport the patient to the radiological imaging device.

At the end of the examination the above operations are performed in reverse order. For example, the containment portion is opened to release said patient and then the sliding means 3 are restored (for example by lowering the sliding means 3 vertically to the floor using the linear movement devices 6), in order to move the supporting device 1 away from the radiological imaging device.

Alternatively, the sliding means 3 are restored (for example by lowering the sliding means 3 vertically to the floor using the linear movement devices 6), the patient, still inside the supporting device for radiological examinations 1, is taken to a suitable place and the containment portion is opened to release said patient.

The disclosed embodiments achieve some important advantages. With the supporting device for radiological examinations 1, placing the patient in position for the examination is a simple operation. It is particularly advantageous for the large animals described previously. Based on experiments conducted by the inventors, such animals do not even have to be sedated to carry out the examination. Another important advantage lies in the fact that with the supporting device for radiological examinations 1, the patient can stand up and can be kept in that position during image acquisition. Furthermore, owing to the presence of the examination portion transparent to X-rays, said images are extremely accurate and clear and are helpful for determining the extent of an injury or examining the part of the body in question.

Modifications and variations may be made to the embodiments described herein without departing from the scope of the inventive concept as expressed in the independent and dependent claims. All details may be replaced with equivalent elements and the scope of the invention includes all other materials, shapes and dimensions.

The invention claimed is:

1. A supporting device for performing radiological examinations on a patient having a part of the body examined, comprising:
    perimeter side members configured to contain the patient along a closed perimeter and at least in a horizontal plane and substantially in contact, when in use, on a plurality of sides of the perimeter with the patient;
    an openable containment portion comprising a portion of the perimeter side members; and
    an examination portion comprising a remaining portion of the perimeter side members, substantially transparent to X-rays, and configured to contain the part of the body to be examined, wherein the examination portion comprises a plurality of elements stacked vertically, each element translatable and removable independently of the other elements.

2. The supporting device of claim 1, not comprising a base or a horizontal support to support the patient.

3. The supporting device of claim 1, further comprising removable wheels configured to permit the movement of the supporting device with respect to the floor.

4. The supporting device of claim 3, further comprising at least one linear movement device configured to move the wheels so that the supporting device can be moved while remaining in contact with the floor through the wheels or substantially anchored to the floor when the wheels are not in contact with the floor.

5. The supporting device of claim 1, wherein the examination portion protrudes, in the horizontal plane, with respect to the containment portion so as to form a portion that, in the horizontal plane, is made of a material that is substantially transparent to X-rays.

6. The supporting device of claim 1, wherein the examination portion defines a wedge-shaped examination wall in the horizontal plane.

7. The supporting device of claim 6, wherein the examination portion protrudes in a direction of exposure with respect to the containment portion, and wherein the examination wall is translatable, in the horizontal plane, in the direction of exposure.

8. The supporting device of claim 1, wherein the elements are configured to be rotated around an axis of rotation substantially parallel to a direction of exposure.

9. The supporting device of claim 1, wherein:
    the perimeter side members are substantially parallelepiped in shape;
    the containment portion substantially defines three walls of the parallelepiped;
    the examination portion defines the remaining part of the parallelepiped; and
    two walls of the containment portion are openable.

* * * * *